United States Patent [19]
Tabler et al.

[11] 4,025,574
[45] May 24, 1977

[54] HYDROCARBON SEPARATIONS

[75] Inventors: Donald C. Tabler; Marvin M. Johnson, both of Bartlesville, Okla.

[73] Assignee: Phillips Petroleum Company, Bartlesville, Okla.

[22] Filed: Nov. 20, 1975

[21] Appl. No.: 633,885

[52] U.S. Cl. .................... 260/677 A; 260/681.5 C
[51] Int. Cl.² ......................................... C07C 7/16
[58] Field of Search ................ 260/677 A, 681.5 C

[56] References Cited
UNITED STATES PATENTS

| | | | |
|---|---|---|---|
| 2,386,358 | 10/1945 | Schultze et al. | 260/681.5 C |
| 3,014,973 | 12/1961 | de Vries et al. | 260/677 A |
| 3,401,112 | 9/1968 | Dunlop et al. | 260/681.5 C |

Primary Examiner—C. Davis

[57] ABSTRACT

A process for the separation and recovery of unsaturated aliphatic hydrocarbons from admixture with saturated aliphatic hydrocarbons which comprises contacting such a mixture with a complexing agent comprising cuprous salts of sulfonic acids and dialkyl phosphates under such conditions that the unsaturated hydrocarbons are preferentially complexed with the cuprous salts. In one embodiment, olefins are separated from paraffins by using a cuprous sulfonate dissolved in an aromatic solvent to form a complex with the olefin. The olefin can be separated from the resulting complex and the cuprous salt recycled for reuse.

6 Claims, No Drawings

HYDROCARBON SEPARATIONS

The present invention relates to a process for the separation and recovery of unsaturated hydrocarbons. In accordance with one aspect, the present invention relates to a process for the separation and recovery of unsaturated aliphatic hydrocarbons from admixture with saturated aliphatic hydrocarbons by contacting with a complexing agent comprising cuprous salts of sulfonic acids and dialkyl phosphates. In accordance with another aspect, this invention relates to the separation of an olefin from a paraffin by selectively forming a complex with the olefin by contacting with a cuprous salt of a sulfonic acid or dialkyl phosphate. In accordance with a further aspect, the invention relates to the formation of a cuprous salt-olefin complex which is treated under conditions to recover the olefin and the cuprous salt which is recycled for reuse.

The separations problem which has required and received considerable attention is that of separating unsaturated aliphatic hydrocarbons such as olefins from close boiling and difficultly separable saturated hydrocarbons such as the paraffins. Many processes have been proposed for such separations including liquid-liquid extraction, extractive distillation, as well as complex formation. With respect to complex formation, various complexing agents have been described in the prior art. The present invention relates to the use of an improved complexing agent exhibiting good selectivity and one that is readily recoverable.

Accordingly, an object of this invention is to provide an improved process for the separation of hydrocarbons.

It is another object of this invention to provide an improved process for the separation of unsaturated aliphatic hydrocarbons from saturated aliphatic hydrocarbons.

Another object of this invention is to provide complexing agents for the separation of olefins from paraffins.

Another object of this invention is to provide a process for the separation of unsaturated hydrocarbons from admixture with saturated hydrocarbons by selectively complexing the unsaturated hydrocarbons from the mixture.

Other objects and aspects, as well as the several advantages of the invention, will be apparent to those skilled in the art upon a study of this disclosure and the appended claims.

In accordance with the invention, a process is provided for the separation of unsaturated aliphatic hydrocarbons from admixture with saturated hydrocarbons by contacting a mixture of saturated and unsaturated hydrocarbons with a complexing agent selected from cuprous salts of sulfonic acids and dialkyl phosphates under such conditions that the unsaturated hydrocarbons are preferentially complexed with the copper salts.

In accordance with one specific embodiment, alkenes and cycloalkenes are separated from admixture with saturated hydrocarbons by contacting with a complexing agent comprising copper (I) salts of sulfonic acids and copper (I) salts of dialkyl phosphates dissolved in a hydrocarbon solvent such as paraffinic and aromatic solvents under conditions such that the unsaturated hydrocarbons are preferentially complexed with the copper salt while the saturated hydrocarbons remain uncomplexed.

Further, in accordance with the invention, the complex resulting from the above separations if further treated under conditions to separate the unsaturated hydrocarbons therefrom and allowing the recycle of cuprous salt for reuse.

The copper (I) salts employed in the present invention are selected from the group consisting of:

a. the copper (I) salt of an alkane sulfonic acid having from 4 to 20 carbon atoms per molecule;

b. the copper (I) salt of an aromatic sulfonic acid including hydroxyaromatic and haloaromatic sulfonic acids having from 6 to 22 carbon atoms per molecule;

c. the copper (I) salt of a petroleum sulfonic acid; and d. the copper (I) salt of a dialkyl phosphate having from 1 to 12 carbon atoms per alkyl member.

The alkane sulfonic acids useful in the practice of this invention can be straight chain or branched. Examples of suitable alkane sulfonic acids include n-butanesulfonic acid, 2-ethyl-1-hexanesulfonic acid, 2-methylnonanesulfonic acid, dodecanesulfonic acid, 2-ethyl-5-n-octyldecanesulfonic acid, n-eicosanesulfonic acid, and the like. A presently preferred alkane sulfonic acid is 2-ethyl-1-hexanesulfonic acid.

The aromatic, hydroxyaromatic, and haloaromatic sulfonic acids useful in the practice of this invention include benzenesulfonic acid, alkylbenzenesulfonic acids wherein the alkyl member contains from 1 to 16 carbon atoms, such as p-toluene-sulfonic acid, p-dodecylbenzenesulfonic acid, p-hexadecylbenzenesulfonic acid, and the like, naphthalenesulfonic acid, phenolsulfonic acid, naphtholsulfonic acids, and halo-benzenesulfonic acids, such as p-chlorobenzenesulfonic acid, p-bromobenzenesulfonic acid, and the like. A presently preferred aromatic sulfonic acid is p-dodecylbenzenesulfonic acid. Commercially available mixtures of o-, m-, and p-dodecylbenzenesulfonic acid can be employed. Preferably, the mixture employed is predominantly, i.e., 85–90 mole percent, the para isomer.

The petroleum sulfonic acids useful in the practice of this invention can be prepared from a deasphalted, solvent-refined petroleum fraction having a viscosity of about 140 to about 720 SUS at 210° F (99° C). A presently preferred sulfonation stock is a propane-fractionated, solvent-extracted, dewaxed Mid-Continent oil of about 200 to 230 SUS at 210° F (99° C) and having a viscosity index of about 90 to 100, or higher. A Mid-Continent oil is more precisely defined as a mixed base or intermediate base oil in "The Science of Petroleum," Volume 1, page 7, Oxford University Press, London, New York, and Toronto, 1938. Such oil is, for example, sulfonated with a 10 percent $SO_3$—90 percent $SO_2$ mixture in a continuous operation substantially as described in U.S. Pat. No. 3,135,693 to Whitney et al, using an $SO_3$ to oil weight ratio of about 0.08 and a reaction temperature of about 115° F (46° C). The total reaction time is about 5 minutes, including the mixing and soaking periods. The system is maintained in the liquid phase at a pressure of 100—120 psig (689—827 kPa gage). Effluent from the reaction unit is subjected to a two-stage flash for $SO_3$–$SO_2$ removal.

The dialkyl phosphates useful in the practice of this invention include dimethyl phosphate, diethyl phosphate, di-n-butyl phosphate, di-2-ethylhexyl phosphate, di-n-dodecyl phosphate, and the like.

The absorbent compositions of the present invention are generally prepared by refluxing a solution of the sulfonic acid or dialkyl phosphate in an inert diluent, as hereinafter described, together with cuprous oxide, with provision for removing the water of reaction, such as Dean-Stark trap. The preparation is carried out in a oxygen-free inert atmosphere such as under nitrogen. The molar ratio of acid to copper is about 1 to 1. The preparation is carried out for a time sufficient to produce substantially complete reaction. The copper (I) salts can, if desired, be separated from the diluent by removing the diluent as by vacuum distillation.

The cuprous salts are normally used at about an 0.5 to 2 molar solution in a hydrocarbon solvent or diluent including paraffinic and aromatic hydrocarbons having from about 5 to about 15 carbon atoms, preferably aromatics such as p-xylene, to produce a solution or slurry of the complexing reagent. The choice of solvent is related to the boiling point of the feedstock, and it is preferably at least 50–60° F (28–33° C) higher than the boiling point of the feedstock. Examples of suitable aromatic solvents include benzene, the alkyl derivatives of benzene, as for example, toluene, the xylenes, isopropyl benzene, 1,3,5-trimethylbenzene, 1,2,4,5,-tetramethylbenzene, hexamethylbenzene, polynuclear aromatic hydrocarbons such as naphthalene, anthracene, and the like. For example, in the separation of normally gaseous olefins having from 2–4 carbon atoms per molecule, p-xylene is presently preferred for dissolving the cuprous salt in forming the reagent. The solvent used in forming the cuprous salt reagent for separation of normally liquid olefins is dictated by the boiling point of the olefin or the feedstock containing it. Para-xylene can also be employed as the solvent for the reagent when $C_5$–$C_7$ olefins are to be separated form paraffins.

Suitable paraffinic solvents that can be used include n-hexane, n-octane, n-decane, and the like. The paraffinic solvents are particularly effective in the separation of cyclic olefins from cyclic paraffins, e.g., the separation of cyclohexene from cyclohexane. A presently preferred solvent for this embodiment of the invention is n-octane. It is also within the scope of the invention to use mixtures of the solvents, i.e., mixtures of aromatics or mixtures of paraffins or mixtures of aromatics and paraffins.

It is desirable to have as much of the copper (I) salt in the absorbent system as possible; the higher the salt/diluent ratio, the greater will be the complexing capacity of the system, and the greater the amount of unsaturated hydrocarbon, e.g., olefin, that can be complexed. Salt/diluent molarities of at least 0.5 mole of salt per liter of diluent have given highly satisfactory results. However, at a molarity of about 2 or more, the solution viscosity can increase enough to cause pumping difficulties, and such viscous solutions are preferably avoided.

The process of the invention is advantageously employed for the separation of mixtures of close boiling aliphatic hydrocarbons having from 2 to about 25 carbon atoms, preferably from 2 to about 10 carbon atoms. Such separations include the separation of olefin hydrocarbons from paraffin and/or naphthene hydrocarbons and the separation of diolefin hydrocarbons from paraffin and/or naphthene hydrocarbons. The process of the invention is particularly suitable for separating aliphatic monoolefins from close boiling saturated hydrocarbons. The process is often utilized for the separation of normally gaseous olefins having from 2–4 carbon atoms from paraffins and the separation of olefins and cycloolefins having from 5–7 carbon atoms from paraffins.

Acyclic and cyclic olefins having from 2 to about 20 carbon atoms per molecule can be separated from paraffins and cycloparaffins by employing the reagent of this invention. Examples include ethylene, propylene, the butenes, 2-pentene, cyclopentene, cyclohexene, cycloheptene, 1-heptene, 1-dodecene, 1-eicosene, 3-methyl-1-butene, 4-methyl-1-pentene, 2,3-dimethyl-2-butene, and the like.

The type of separation contemplated in this invention is the separation of alkenes and cycloalkenes from a paraffin or several paraffins, all components of the mixture having similar boiling points. Examples include the separation of ethylene from ethane, propylene from propane, 1-octene from n-octane, cyclohexene from cyclohexane, and the like.

The advantages of employing the cuprous salts of this invention over other cuprous compounds such as cuprous tetrachloroaluminate are numerous. These include low corrositivity of process equipment, particularly those fabricated from stainless steel, and water tolerance. In addition, the cuprous salts of this invention, depending upon the nature of the hydrocarbon portion of the molecule, are soluble in both aromatic and paraffinic hydrocarbon solvents whereas the previously referred to cuprous salt is soluble in aromatic hydrocarbons by virtue of forming weak pi-complexes with the aromatic, hence it is not expected to be soluble in aliphatic hydrocarbons. The presently preferred cuprous salt of this invention, i.e., copper (I) dodecylbenzene sulfonate, also forms a weak pi-complex, but this is apparently not the only mechanism of solubility because the cuprous sulfonate is also soluble in aliphatic hydrocarbons.

The conditions employed in practicing this invention are selected to allow the olefin to react with the complexing reagent to form the complex while minimizing the problem of separating the nonreacted or noncomplexed portion of the feedstream. In the absorption zone, an absolute pressure ranging from about 0.05 to 20 atmospheres (0.05 to 2 MPa), more preferably from about 0.05 to 2 atmospheres (0.05 to 0.02 MPa), and a temperature ranging from about −10° C to about 10° C below the boiling point of the solution or slurry of the complexing reagent, preferably from about 30° C to about 25° C below the boiling point of the complexing reagent, can be used.

In the desorption zone, the conditions are selected sufficiently different from those used in the absorption zone to promote desorption. Thus, an absolute pressure ranging from about 0.1 to 1.5 atmospheres (0.01 to 0.15 MPa), more preferably from about 0.5 to 1 atmosphere (0.05 to 0.1 MPa), can be employed. The temperature in this zone can range from about 50° C below the boiling point of the solution or slurry of the reagent to the boiling point of the solution or slurry, more preferably from about 30° C below the boiling point of the solution or slurry of the reagent to the boiling point of the solution or slurry.

EXAMPLE I

A gaseous blend of ethylene and ethane was prepared in a 250 ml steel sample bomb by charging the evacuated bomb with ethylene up to 20 psig (138kPa) and then on up to 114 psig (786 kPa) with ethane. The absolute pressure contributed by the ethylene in the mixture is about 20 + 14.7 or 34.7 psia. Similarly, since the total pressure is 114 + 14.7 or 128.7 psig, the ethane contribution is calculated to be 128.7 - 34.7 or about 94 psia. The fraction of ethylene in the mixture, assuming ideal gases, thus constitutes about 27 mole percent.

250 ml of the gaseous blend was bubbled through a 0.4 molar solution of copper (I) dodecylbenzene sulfonate in P-xylene at 26.8° C and 738.8 mm Hg pressure. The effluent gas was stored in a 250 ml glass bomb. Another 250 ml portion of the gas mixture was bubbled through the reagent as before and the off-gas in a separate 250 ml glass bomb. Analysis of the effluent gas samples by gas-liquid chromatography revealed that the composition of the first effluent was 99.675 mole percent ethane and 0.325 mole percent ethylene, and the composition of the second effluent was 99.951 mole percent ethane and 0.049 mole percent ethylene. The results demonstrate the effective separation of the two constituents. The ethylene could be recovered from the copper complex by stripping it off at the boiling point of the solution or slurry of the reagent.

EXAMPLE II

The separation of cyclohexene from cyclohexane contained in an n-octane solvent is demonstrated in this example.

A solution containing about 20 weight percent cyclohexene and about 80 weight percent cyclohexane was prepared. 28 g of the blend was mixed with 152 ml of a 0.6 molar solution of copper (I) dodecylbenzene sulfonate in n-octane. The mixture was heated to boiling, and a batch distillation was carried out. Cuts of the condensing hydrocarbon mixture were taken and analyzed by gas-liquid chromatography. The results are presented in Table I.

TABLE I

| Separation of Cyclohexene from Cyclohexane | | | | | | | | |
|---|---|---|---|---|---|---|---|---|
| Run No.: | 1 | 2 | 3 | 4 | 5 | 6 | 7 | 8[(b)] |
| Overhead Liquid, ml | 20 | 20 | 20 | 8 | 20 | 20 | 12[(a)] |  |
| Overhead Liquid, g | 14.9 | 14.6 | 14.4 | 5.5 | 13.8 | 13.8 | 8 | 0 |
| Cyclohexane, Wt. % | 43.78 | 35.04 | 24.34 | 15.55 | 4.95 | 1.63 | 0.38 | 79.31 |
| Cyclohexene, Wt. % | 2.20 | 2.14 | 2.19 | 2.34 | 2.31 | 2.31 | 4.37 | 20.37 |
| n-Octane, Wt. % | 53.84 | 62.68 | 73.35 | 82.10 | 92.70 | 96.06 | 95.24 | 0 |
| Others, Wt. % | 0.18 | 0.14 | 0.13 | nd[(c)] | 0.03 | nd | 0.01 | 0.32 |
| Cyclohexane, Wt. ratio / cyclohexene | 19.9 | 16.4 | 11.1 | 6.6 | 2.1 | 0.70 | 0.087 | 3.89 |
| Wt. % $C_6$ in cut | 45.98 | 37.18 | 26.53 | 17.89 | 7.26 | 3.94 | 4.75 | na[(d)] |
| Wt. % cyclohexene in $C_6$ | 4.78 | 5.76 | 8.25 | 13.10 | 31.82 | 58.6 | 92.0 | na |

[(a)]Most of volatile hydrocarbon has been removed from the kettle. Vapor flow overhead stopped.
[(b)]Analysis of hydrocarbon feed.
[(c)]None detected.
[(d)]Not applicable.

The results presented show that the cyclohexane/cyclohexene weight ratio of runs 1–4 are higher than control run 8 indicating that a relative enrichment of cyclohexane is occurring. Run 1 is especially significant because of the pronounced cyclohexane enrichment. This means that much of the cyclohexene is tied up as a complex with the copper reagent. As the ratio declines with continued heating and more cyclohexene appears overhead, the results show that the copper reagent-olefin complex is reversible in nature. The significance of this means that a separation between cyclohexene and cyclohexane can be accomplished under absorption conditions. The effluent from the absorption zone can be passed to a stripping zone where the pure cyclohexene is separated and the regenerated copper reagent can be recycled to the absorption zone.

We claim:

1. A process for the separation of unsaturated aliphatic hydrocarbons having from 2 to about 25 carbon atoms from admixture with saturated hydrocarbons comprising contacting a mixture of saturated and said unsaturated hydrocarbons with a 0.5 to 2 molar solution of a copper (I) salt of an alkylbenzenesulfonic acid wherein the alkyl group contains from 1 to 16 carbon atoms in a hydrocarbon solvent selected from paraffinic and aromatic hydrocarbons having from 5 to about 15 carbon atoms under such conditions that said unsaturated hydrocarbons are preferentially complexed with said copper (I) salt while the saturated hydrocarbons remain uncomplexed, and recovering said unsaturated hydrocarbons from the resulting complex containing same.

2. A process according to claim 1 wherein the complex containing said unsaturated hydrocarbon is separated from the uncomplexed hydrocarbon, and the complexed unsaturated hydrocarbon is desorbed from the complex by subjecting the complex to at least one of decompression or heating.

3. A process according to claim 1 wherein said unsaturated hydrocarbons are acyclic and cyclic olefins having from 2 to about 20 carbon atoms per molecule and said copper (I) salt is dissolved in an aromatic solvent.

4. A process according to claim 3 wherein said unsaturated hydrocarbons are olefins and cycloolefins having from 2–10 carbon atoms.

5. A process according to claim 1 wherein said unsaturated hydrocarbon is ethylene, said salt is copper (I) dodecylbenzene sulfonate, and said salt is dissolved in p-xylene.

6. A process according to claim 1 wherein said unsaturated hydrocarbon is cyclohexene, said salt is copper (I) dodecylbenzene sulfonate, and said salt is dissolved in n-octane.

* * * * *